United States Patent [19]
Hill

[11] Patent Number: 6,024,726
[45] Date of Patent: Feb. 15, 2000

[54] MIDDLE EAR FLUID ASPIRATOR

[76] Inventor: Frank C Hill, 10 Brandywine Ln, Columbia, S.C. 29206

[21] Appl. No.: 09/207,695

[22] Filed: Dec. 8, 1998

Related U.S. Application Data

[60] Provisional application No. 60/099,299, Aug. 25, 1998.

[51] Int. Cl.$^7$ ..................................................... A61M 5/00
[52] U.S. Cl. ......................... 604/187; 604/239; 604/240; 604/540; 604/35; 604/117
[58] Field of Search ..................... 604/187, 239, 604/240, 540, 317, 43, 44, 45, 117, 35, 181, 272, 149, 289, 294; 600/573, 576, 578, 579, 581

[56] References Cited

U.S. PATENT DOCUMENTS

| | | |
|---|---|---|
| 3,018,779 | 1/1962 | Tyler et al. . |
| 4,775,366 | 10/1988 | Rosenblatt . |
| 4,813,433 | 3/1989 | Downey . |
| 4,861,332 | 8/1989 | Parisi ......................................... 604/35 |
| 4,958,622 | 9/1990 | Selenke . |
| 4,995,867 | 2/1991 | Zollinger . |
| 5,032,111 | 7/1991 | Morris et al. .............................. 604/43 |
| 5,062,835 | 11/1991 | Maitz et al. . |
| 5,069,665 | 12/1991 | Ng . |
| 5,086,782 | 2/1992 | Zucker . |
| 5,110,557 | 5/1992 | Brown et al. . |
| 5,167,622 | 12/1992 | Muto ....................................... 604/540 |
| 5,188,617 | 2/1993 | Linder ..................................... 604/117 |
| 5,201,718 | 4/1993 | Whisson ................................... 604/240 |
| 5,263,942 | 11/1993 | Smidley et al. ......................... 604/240 |
| 5,396,899 | 3/1995 | Strittmatter . |
| 5,405,321 | 4/1995 | Reeves .................................... 604/540 |
| 5,665,094 | 9/1997 | Goldenberg . |
| 5,792,099 | 8/1998 | DeCamp et al. ........................ 604/240 |
| 5,817,075 | 10/1998 | Giungo .................................... 604/297 |

*Primary Examiner*—Corrine McDermott
*Assistant Examiner*—Jeremy Thissell
*Attorney, Agent, or Firm*—Michael A. Mann; Nexsen Pruet Jacobs & Pollard LLP

[57] ABSTRACT

A middle ear fluid aspirator comprised of a syringe assembly that provides suction through the creation of negative pressure therein and a needle having an angled region that permits the operation of the aspirator while maintaining visual contact with the tympanic membrane and a needle safety assembly whereby the penetrating portion of the needle is not capable of damaging the ossicular structures of the ear.

13 Claims, 2 Drawing Sheets

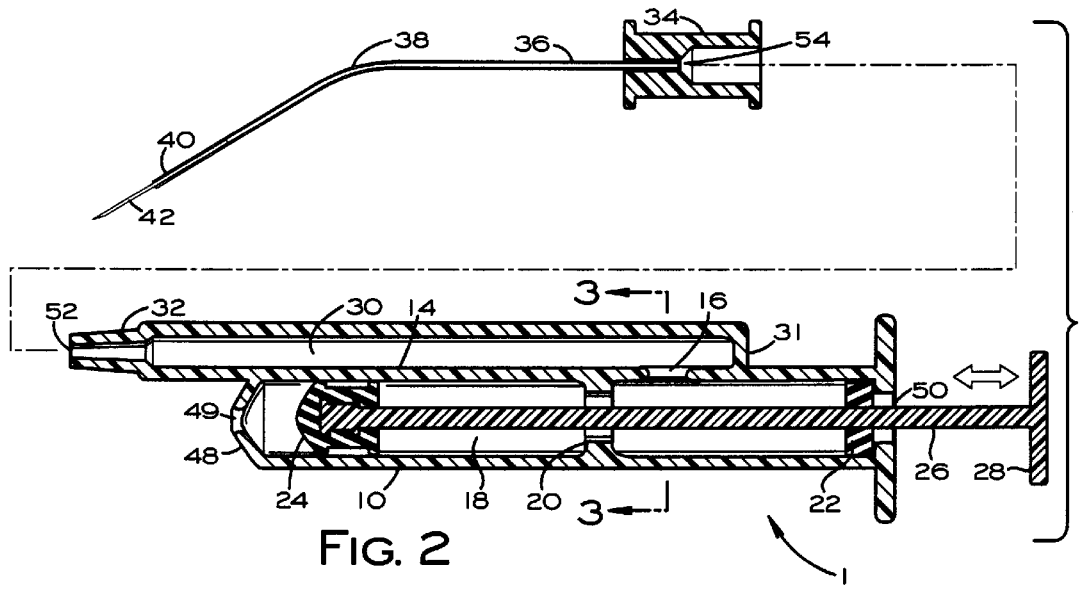
FIG. 2
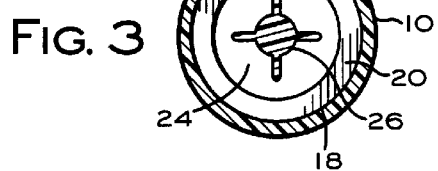
FIG. 3
FIG. 4
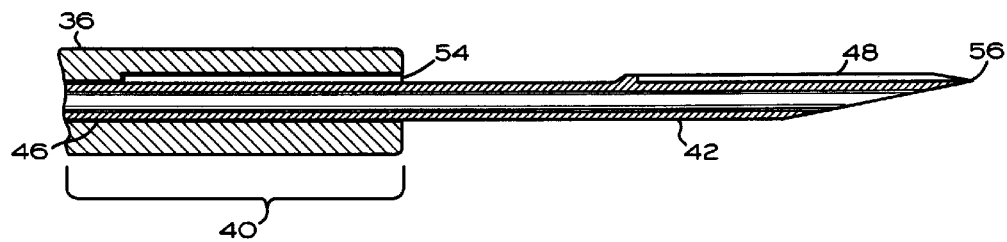

6,024,726

MIDDLE EAR FLUID ASPIRATOR

This application claims the benefit of U.S. Provisional Application No. Ser. 60/099,299, filed on Aug. 25, 1998.

1. FIELD OF THE INVENTION

The present invention relates to aspirators, and, in particular, to aspirators for removing fluid from the middle ear.

2. BACKGROUND OF THE INVENTION

Infections of the middle ear present an ongoing problem to both patients who suffer from them as well as to treating physicians who seek to treat them. To the patient, these infections represent acute pain, discomfort, financial cost and/or possible loss of hearing. To the treating physician, these infections present significant dilemmas. Since middle ear infections have been heretofore difficult to treat with medications, the treating physician had basically two therapeutic alternatives. The primary care physician may either tap the middle ear or refer the patient to an ear, nose and throat specialist so that a tympanocentesis or insertion of tubes may be employed. In order to the tap the middle ear, the physician has utilized suction or conventional syringes which have several attendant disadvantages. Suction assemblies are often not available and are cumbersome to use. Conventional syringes have required the physician to actuate the syringe by pulling back on the plunger. The syringe assembly of the present invention, on the other hand, is disposed so that when the plunger is pressed the syringe assembly is actuated thereby providing increased control by the operator. Further, if the needle of the syringe is straight, as is usually the case, then the syringe interferes with the operator's line of vision. The syringe assembly of the present invention, on the other hand, has the advantage that it may be operated through an otoscope thereby providing the operator with a clear line of sight. A common danger with pre-existing syringe needles is that there is no guard against the operator accidentally penetrating the tympanic membrane in such a way as to cause damage to the bony structures there within. The needle of the present invention is provided with a safety assembly whereby the needle recedes or deforms if it comes into contact with bony structures.

The middle ear fluid aspirator of the present invention provides significant advantages over prior the prior art and incorporates safety features which protect the patient. The objectives, features, and advantages of the present invention are apparent upon consideration of the following specification and the appended drawings.

SUMMARY OF THE INVENTION

In view of the foregoing, a first aspect of the invention is a middle ear fluid aspirator comprising a syringe assembly and needle wherein the syringe assembly operates via negative pressure in order to provide suction through the needle when the plunger is pushed and a needle having an angled or curved region, which permits the operator to operate the middle ear fluid aspirator while having visual contact with the tympanic membrane, and further having a safety assembly which permits for the penetrating portion of the needle to recede into the non-penetrating portion of the needle when the penetrating portion of the needle comes into contact with bony structure within the middle ear. Alternative safety designs, such as a thin-walled needle that deforms when it contacts bone also falls within the scope of this invention. The penetrating portion of the needle is additionally provided with a canal that allows for pressure equalization within the middle ear when fluid is aspirated.

The foregoing and other aspects of the present invention are explained in detail in the specification set forth below.

BRIEF DESCRIPTION OF THE DRAWINGS

FIG. 2 is a perspective view of the syringe assembly and syringe needle of the middle ear fluid aspirator of the present invention.

FIG. 3 is a cross-sectional view of the syringe assembly of the middle ear aspirator of the present invention along the 3—3 line.

FIG. 4 is a perspective view of the syringe needle safety assembly.

FIG. 5 is a perspective of the penetrating needle disposed through the tympanic membrane and in the middle ear.

FIG. 6 is a cross-sectional view of the penetrating needle along the 6—6 line.

DESCRIPTION OF THE PREFERRED EMBODIMENTS

Figure 1:
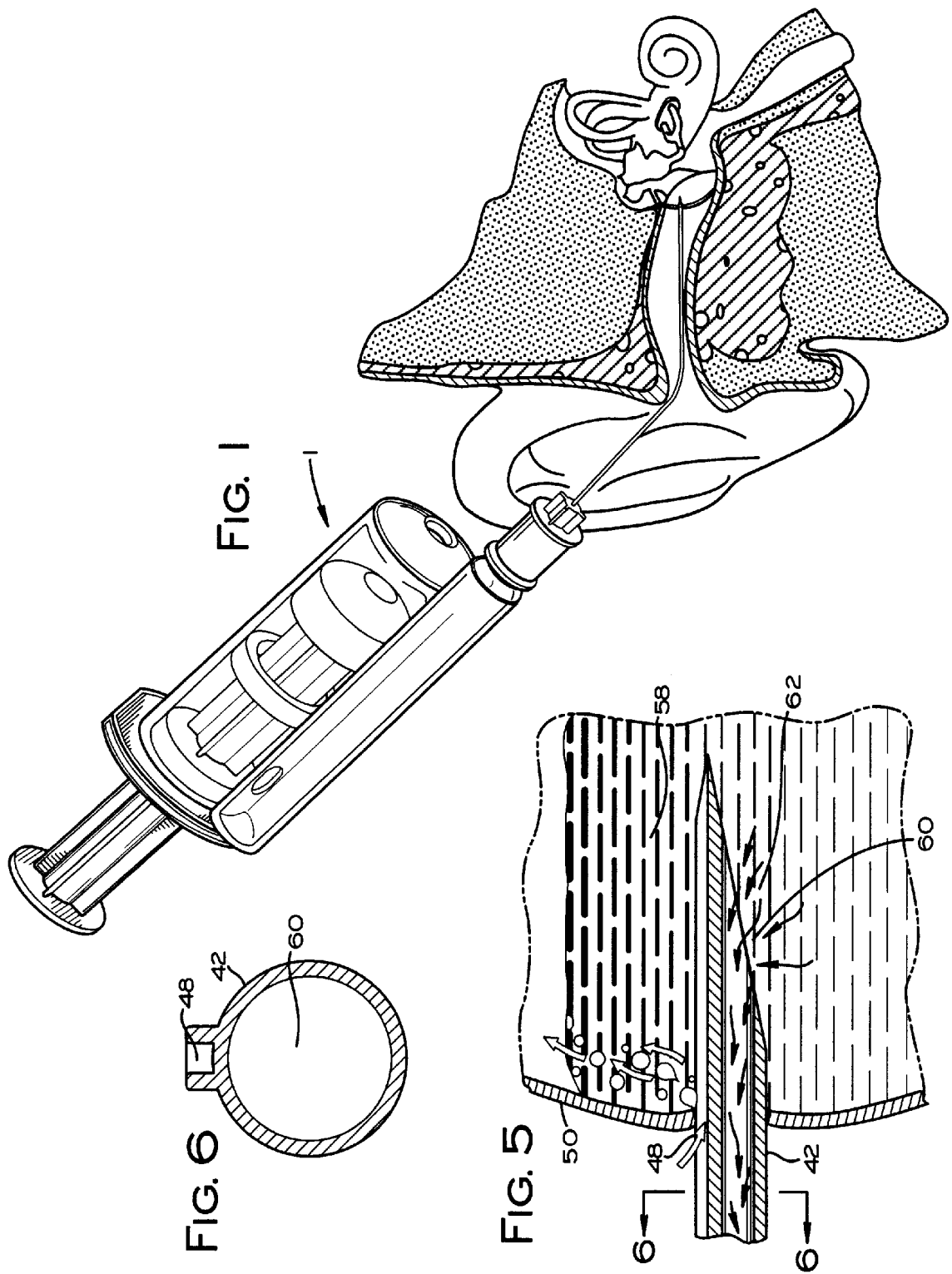
FIG. 1 is a sectional view of the middle ear fluid aspirator of the present invention in place through the tympanic membrane of a patient.

With reference to FIG. 1, the syringe assembly of the present invention is identified by the numeral 1 and is shown in place within the ear canal of a patient. The tip of the syringe needle is shown penetrating the tympanic membrane so that fluid accumulated within the middle ear may be extracted by use of the syringe of the present invention.

With reference to FIG. 2, the syringe assembly 1 is shown to be comprised of a housing 10, a partition 14, dividing the said housing into a first compartment 18 and a second compartment 30, an opening 16 connecting said first compartment 18 to said second compartment 30, a piston 24, disposed in said first compartment 18, attached to shaft 26, a first end wall 48, having a port 49, disposed at the end of said first compartment 18, a seal means 22, a slide stop 20, a needle hub 32 disposed on said second compartment 30.

The housing 10 is generally cylindrical in shape and may be made of any suitable translucent material such as glass, plastic, or the like. Housing 10 is divided into a first compartment 18 and second compartment 30, by partition 14, first end wall 48 having a port 49 for the egress of air, second end wall 31, seal means 22. First compartment 18 is connected to second compartment 30 by opening 16. Disposed within first compartment 18 is piston 24 which is attached to shaft 26. Shaft 26 extends through seal means 22 and through aperture 50 and is attached to handle 28. As the operator applies pressure to handle 28, shaft 26 forces piston 24 to move from an initial position adjacent to and in contact with slide stop 20 towards end wall 48. Such movement causes negative pressure behind the piston 24 and thereby causes flow into said second compartment 30 through aperture 52. Piston 24 and seal means 22 are made of any suitable material which is inert and provides an airtight connection with the walls of first compartment 18 and with shaft 26 such that piston 24 maintains an airtight, frictional, sliding relationship to the walls of first compartment 18.

Needle hub 32 provides an anchoring location for needle anchoring means 34 such that needle 36 may be attached to syringe assembly 1 at needle hub 32 in an airtight fashion in which the lumen 54 of said needle 36 is in contact with second compartment 30 allowing for flow of fluids from the lumen 54 through aperture 52 into second compartment 30. Needle 36 is provided with angled region 38 allowing for use insertion of said needle 36 into the ear canal of a patient while allowing the user visual access to the tympanic membrane. Angled region 38 is bent to a suitable degree for use with an otoscope, and may range from about 60° to about 30°, preferably about 45°. Needle 36 is further provided with safety assembly 40 and penetrating needle 42.

With reference to FIG. 3, a cross-sectional view of syringe assembly 1 along axis 3 wherein first compartment 18 is shown in relationship to second compartment 30 within housing 10. In first compartment 18 can be seen slide stop 20 and extending therethrough shaft 26 which is anchored to piston 24.

With reference to FIG. 4, the safety assembly 40 is shown in which the penetrating needle 42 extends into the lumen 54 of needle 36 in a frictional, airtight relationship with the interior surface 46 of lumen 54 such that penetrating needle 42 may slide further into lumen 54 in the event penetrating needle tip 56 encounters resistance such as from bony structures with the middle ear. Upon encountering such resistance penetrating needle 42 would then slide further into lumen 54 thereby eliminating the danger of damaging any such bony structures within the middle ear. Penetrating needle 42 is provided with canal 48 permitting air contact between the ear canal and the middle ear when penetrating needle 42 penetrates the tympanic membrane. An alternative embodiment, not shown, would comprise a thin-walled penetrating needle portion that permits penetration of the tympanic membrane while deforming if it contacts bony structures within the middle ear. It will be obvious to those skilled in the art that other alternative embodiments which prevent damage to ossicular tissues of the ear are available and fall within the scope of the invention.

With reference to FIG. 5, penetrating needle 42 is shown disposed through tympanic membrane 50 and into the middle ear cavity 58 allowing for fluid 62 to be aspirated through penetrating needle lumen 60. Canal 48 allows for the flow of air into said middle air cavity 58 when fluid 62 is aspirated. The canal 48 allows for pressure equalization when fluid is being aspirated through penetrating needle 42.

With reference to FIG. 6, a cross-sectional view of penetrating needle 42 is shown along axis 6 and illustrates penetrating needle 42, penetrating needle lumen 60, and canal 48.

While the present invention has been described with respect to embodiments, it will be understood that various modifications and variations will occur to those skilled in the art from the foregoing detailed description and the accompanying drawings. Such modifications and variations are intended to fall within the scope of the appended claims.

What is claimed is:

1. An aspirator for extracting fluids from a middle ear, said aspirator comprising:

a housing having a compartment and an aperture;

a hollow penetrating needle carried by said housing at said aperture, said hollow penetrating needle having a bore extending longitudinally therethrough, said bore being in fluid communication through said aperture with said compartment, said hollow penetrating needle halving a curved portion so that, as said hollow penetrating needle is inserted by an operator into a middle ear having fluid, the operator has a clear line of sight to said middle ear;

a handle carried by said housing and movable with respect to said housing; and extraction means responsive to pushing of said handle toward said housing for applying a negative pressure to said compartment so that, when said needle penetrates said middle ear and said handle is moved, said fluid is drawn through said needle into said compartment.

2. The aspirator as recited in claim 1, said hollow penetrating needle further comprising a canal so that, as said fluid is drawn through said needle into said compartment, said canal allows a flow of air into said middle ear as said fluid is drawn through said needle from said middle ear so that pressure in said middle ear equalizes.

3. The aspirator as recited in claim 1, said aspirator further comprising a safety assembly carried by said housing, said safety assembly having a longitudinal hole extending therethrough that is dimensioned to hold said needle telescopically to said housing so that said needle will slide into said safety assembly if said needle encounters a bony structure within the middle ear.

4. The aspirator as recited in claim 1, wherein said curved portion is angled between 30 to 60 degrees.

5. The aspirator as recited in claim 1, wherein said curved portion is angled at approximately 45 degrees.

6. The aspirator as recited in claim 1, wherein said hollow penetrating needle is formed to deform upon contact of said needle with bone but not with an ear drum.

7. An aspirator for extracting fluids from a middle ear, said aspirator comprising:

a housing having a compartment and an aperture;

a hollow penetrating needle carried by said housing at said aperture, said hollow penetrating needle having a bore extending longitudinally therethrough, said bore being in fluid communication through said aperture with said compartment, said hollow penetrating needle having a canal formed thereon, said hollow penetrating needle being formed to deform upon contact with bone but not an eardrum;

a handle carried by said housing and movable with respect to said housing; and extraction means responsive to movement of said handle with respect to said housing for applying a negative pressure to said compartment so that, when said needle penetrates into a middle ear having fluid and said handle is moved, said fluid is drawn through said needle into said compartment.

8. The aspirator as recited in claim 7, wherein said hollow penetrating needle has sufficiently thin walls to deform upon contact with a bony structure within the middle ear.

9. The aspirator as recited in claim 7, wherein said hollow penetrating needle has a curved portion so that as said hollow penetrating needle is inserted by an operator into a middle ear having fluid, the operator has a clear line of sight to said middle ear, said curved portion angled between 30 to 60 degrees.

10. A fluid aspirator for extracting fluids from a middle ear, said aspirator comprising:

a housing having a compartment and an aperture;

a hollow penetrating needle having a bore extending longitudinally therethrough, said bore being in fluid communication with said compartment;

a safety assembly carried by said housing, said safety assembly having a longitudinal hole extending therethrough that is dimensioned to hold said needle telescopically to said housing so that said needle will slide into said safety assembly if said needle encounters a bony structure within the middle ear;

a handle carried by said housing and movable with respect to said housing; and extraction means responsive to movement of said handle with respect to said housing so that, when said needle penetrates into a middle ear having fluid and said handle is moved, said fluid is drawn through said needle into said compartment.

11. The aspirator as recited in claim 10, wherein said hollow penetrating needle has curved portion so that as said hollow penetrating needle is inserted by an operator into a middle ear having fluid, the operator has a clear line of sight to said middle ear.

12. The aspirator as recited in claim 10, wherein said hollow penetrating needle has a canal, said canal allowing a flow of air into said middle ear as said fluid is drawn through said needle from said middle ear so that pressure in said middle ear equalizes.

13. The aspirator as recited in claim 10, wherein said hollow penetrating needle has a curved portion so that as said hollow penetrating needle is inserted by an operator into a middle ear having fluid, the operator has a clear line of sight to said middle ear, said curved portion angled between 30 to 60 degrees.

* * * * *